United States Patent [19]  [11]  4,219,543
Hartmann et al.  [45]  Aug. 26, 1980

[54] CHANNEL CATFISH VIRUS DISEASE VACCINE AND METHOD OF PREPARATION THEREOF AND METHOD OF IMMUNIZATION THEREWITH

[75] Inventors: James X. Hartmann, Boca Raton; Edward J. Noga, Lake Worth, both of Fla.

[73] Assignee: Florida Atlantic University, Boca Raton, Fla.

[21] Appl. No.: 40,108

[22] Filed: May 18, 1979

[51] Int. Cl.² ............................................... A61K 39/12
[52] U.S. Cl. ...................................... 424/89; 435/235; 435/237
[58] Field of Search ................... 424/89; 435/235, 237

[56] References Cited
U.S. PATENT DOCUMENTS 4,009,259  2/1977  Ament et al. ........................... 424/89

OTHER PUBLICATIONS

Bowser, P. R., Development and Evaluation of a New Cell Line from the Channel Catfish, Ktalurus Punctatus Ph.D (1978) Diss. Abs. Intl. 39(9), Sec. B, p. 4120.
Glenn, J. S., The Immune Response of the Channel Catfish (Ictalurus Punctatus) Ph.D (1974) Diss. Abs. Intl. 35(10), Sec. B, p. 5199.
Austen, J. D., Pathogenesis of Channel Catfish Virus Disease and Characterization of the Virus Ph.D (1977) Diss. Abs. Int. 38(11), Sec. B, p. 5187.
Schachte, J. H., Studies on the Immunization of the Channel Catfish against Two Bacterial Pathogens Ph.D (1976) Diss. Abs. Int. 37(5), Sec. B, p. 2030.

Primary Examiner—Shep K. Rose
Attorney, Agent, or Firm—Harold L. Stowell

[57] ABSTRACT

The invention relates to a channel catfish virus vaccine comprising an attenuated strain or strains of channel catfish virus and a pharmaceutically acceptable diluent and a method of preparation thereof comprising the serial passage of a channel catfish virus through a plurality of tissue cell cultures until the resulting virus material is sufficiently attenuated to permit its safe administration to channel catfish. The invention also relates to a method of immunizing channel catfish from channel catfish virus disease comprising hyperosmotically infiltrating the channel catfish with the above-described vaccine followed by a the hyperosmotic infiltration thereof with a booster dose of said vaccine.

16 Claims, No Drawings

CHANNEL CATFISH VIRUS DISEASE VACCINE AND METHOD OF PREPARATION THEREOF AND METHOD OF IMMUNIZATION THEREWITH

BACKGROUND OF INVENTION

Channel catfish virus (CCV) disease is a highly virulent and communicable disease of fry and fingerling channel catfish (*Ictalurus punctates Raf.*) which was discovered by Fijan in 1968. (Bull. Off. Int. Epizoot., 69: 1167-68, 1968). Presently, the geographical range of the disease extends from West Virginia to California and Alabama to Nebraska. Since its isolation, the number of states in which epizootics have occurred have increased from four to at least eleven states and one foreign country. Continued extension of the range of the disease is a real possibility since survivors of an epizootic may become asymptomatic carriers from whom virus cannot be isolated.

Mortality rates may range from less than 50% to 100% in affected tests. The highest percentage mortality occurs during the first summer of life when the fish weigh less than 10 g and are less than 10 cm in length. As the fish become larger, the mortality may be reduced and the disease prolonged; but epizootics have occurred in ponds where over 99% of 50,000 5-6 cm fingerlings died in less than one week. (Plumb, J. A. *The Catfish Farmer and World Aqua. News*, 6 (3): 40-42 (1974).

Considering the increasing importance of the channel catfish as a food source, the desirability of obtaining a vaccine for CCV to prevent the economic loss in private and federal hatcheries is evident. CCV is considered to be one of the eight most serious communicable diseases of fish in North America. The disease is probably more prevalent than indicated in the literature since commercial farms are reluctant to report outbreaks due to a fear of suffering business losses as regular and prospective customers might fear introduction of the disease into their facilities.

The culture of channel catfish as a protein source for human and animal consumption is a highly profitable, international business. A vaccine which would protect against the highly devastating effects of CCV disease is very desirable for a number of reasons. First, there is no known treatment of the disease—diseased fish and broodstock are necessarily destroyed at great cost and loss of time. Second, control of the disease is practiced through avoidance, quarantine and disinfection. However, this approach is costly and of limited values since asymptomatic carries of the disease may re-introduce it into a population.

SUMMARY OF THE INVENTION

There is provided according to the present invention a modified, live, infectious channel catfish virus vaccine which imparts immunity from channel catfish virus disease when administered to channel catfish comprising an attenuated strain or strains of channel catfish virus and a pharmaceutically acceptable diluent.

The invention also provides a method of producing an attenuated strain or strains of channel catfish virus comprising:
(a) forming a plurality of catfish tissue cell cultures,
(b) serially passing a virulent channel catfish virus through the cultures for a plurality of passages,
(c) continuing the serial passages until the resulting virus material is attenuated to permit its safe administration to channel catfish,
(d) inoculating catfish tissue cells with the resulting virus material, and
(e) harvesting attenuated virus material from the cells.

The invention also includes a method of immunizing channel catfish from channel catfish virus disease comprising hyperosmotically infiltrating channel catfish with the above-described vaccine and, approximately 45 to 60 days thereafter, again hyperosmotically infiltrating the channel catfish with the vaccine.

DETAILED DESCRIPTION OF THE INVENTION

The vaccine according to the invention is prepared by serial passage of a virulent channel catfish virus through a plurality of catfish tissue cell cultures. It is preferred to employ tissue cell cultures from the walking catfish (*Clarias batrachus* (L.)). It is especially preferred to employ liver, gonad, kidney, spleen and gill tissue cell cultures from the walking catfish. Optimum results are achieved by employing kidney tissue cell cultures.

The following procedures were employed to prepare the vaccine according to the invention.

Walking catfish were collected with bag seines or by electro-shocking. Fish were maintained prior to use in 36 liter (10 gallon) or 72 liter (20 gallon) aquaria with aeration provided by compressed air, and were fed a daily ration of commercial catfish chow at the rate of 1-2% of body weight. Fish used for the initiation of cell cultures weighed at least 50 g.

Fish were sacrificed, their ventral surface disinfected with 70% ethanol, and a longitudinal incision made, exposing the internal organs. The liver, gonad, kidney and spleen were then removed and placed into individual petri dishes.

A modification of the procedure described by McKenzie and Stephenson (P. F. Kruse et al, Eds. Tissue Culture, Academic Press, N.Y. 143-146, (1973) was used to establish primary cultures. A small amount of Puck's Saline G (Merchant et al., *Handbook of Cell and Organ Culture*, Burgess Pub. Co., (1964), without calcium or magnesium (CMF), was added to the tissues in the petri dishes, after which they were minced into fine pieces with a pair of scalpels. The fragments were transferred to 16×125 mm test tubes and washed with four volumes of CMF. Washing was repeated until the supernatant fluid was no longer cloudy. Four volumes of 0.25% Trypsin in CMF were then added to each tube and each was mixed well, normally producing a cloudy supernatant, except in the case of gonadal tissue where few cells or tissue fragments were released. The supernatant was then decanted and fresh trypsin was added. The procedure was repeated 3-4 times.

During initial attempts to establish primaries, cell culture medium was added prior to the plating of the tissue into 25 $cm^2$ plastic tissue culture flasks. These were then placed in an upright position for up to two hours in order to allow the tissue fragments to adhere. In later experiments, culture medium was added after the fragments had been plated. After plating, cultures were incubated at 25° C.

A different procedure was used for culturing gill tissues. Opercula were removed and excised gill fragments were washed twice with four volumes of CMF in a 3 ounce prescription bottle to remove blood and debris. The fluid was replaced with culture medium containing penicillin G (400 units/ml), streptomycin sulfate (400 mcg/ml) and amphotericin B (10 mcg/ml), and the tissue agitated on a rotary shaker at 110 RPM for 24 hr. The medium was changed and this procedure repeated. The arches were then cut into small pieces with a pair of scalpels and plated into a tissue culture flask by standing the flask upright for about 1.5 hr. The fragments were then flooded with culture medium and incubated at 25° C.

The medium for Clarias cell cultures consisted of a modified Ham's F-12 in which all components were present at 52% of the standard recommended concentration. Additionally, the medium contained 23 mM HEPES buffer, 25 mM sodium bicarbonate, 9% fetal bovine serum, and the antibiotics penicillin G (200 units/ml), streptomycin sulfate (200 mcg/ml) and amphotericin B (5 mcg/ml).

Culture medium for the Brown Bullhead (BB) continuous cell line used for assay purposes and for propagation of some viral stocks consisted of MEM (Hank's base) supplemented with 4 mM sodium bicarbonate and 9% fetal bovine serum. Antibiotic concentrations were half those used for the Clarias cells.

Medium was changed on the primary cultures once or twice a week. When the cultures become confluent, cells were removed using a standard trypsinization procedure which was used throughout these experiments. The cell sheets were washed twice with CMF for 5 minutes each, after which 0.5 ml of 0.25% trypsin was added to each culture (i.e., usually 10% of the original culture volume). After the cells had detached, an aliquot was removed and fresh medium was added except after the first trypsinization of the primaries when no cells were removed. Subsequently, cultures were split 1:2 every 4–7 days after reaching confluency.

Brown bullhead cells were also routinely subcultured in 75 $cm^2$ plastic flasks or 50 $cm^2$ glass tissue culture bottles. They were usually expanded about 1:3 or 1:4 when needed. Observations of cultures were made with a Nikon Model MSD Inverted Phase Contrast Microscope.

The various virus strains used herein and their passage histories are as follows:

CCV(AT)-X—Strain Auburn 1 Clone A CCV (ATCC VR #59) isolated by Fijan (Bull, Off. Int. Epizoot. 69: 1167–68, (1968) from an epizootic in southern Alabama. This virus sample has been passaged six times in BB cell culture and had been frozen at this level by the American Type Culture Collection, which corresponded to the third passage of the clone. It was passaged an additional X number of times undiluted in BB cells at a culture medium:inoculum ratio of 100:1 and then frozen at −59° C.

CCV(A)-X—Strain Auburn derived initially from the same isolate as CCV(AT)-X. When received, it had been passaged in cell cultures approximately 30 times, usually with a small inoculum of 0.1 ml of a $10^{-3}$ to $10^{-5}$ dilution per 1–5 ml of culture medium. It was passaged an additional X number of times undiluted in BB cells, usually at an inoculum:culture medium ratio of 1:100.

VX (K1K)—Auburn Strain CCV derived from CCV(A)-3 and passaged X times in Clarias K1K cells.

CCV(JXH)-1—Produced by inoculating a 50 cm BB culture with 0.1 ml of a CCV(A)-5 sample. When CPE was almost complete, the culture was frozen and thawed 3X by alternately placing the bottle at −59° C. for about 15 minutes and then thawing to a liquid at room temperature. 1–2 ml aliquots were then frozen at −59° C.

CCV(H)-2—A strain of CCV isolated from an epizootic which occurred at Homestead Fisheries, Homestead, Florida, in July 1977. This virus sample was isolated in BB cells in a 16×125 mm culture tube from a bacteria-free filtrate of infected channel catfish fry. 0.1 ml of the infected culture was then added to a $50^2$ cm bottle of BB cells. When about 90% of the cells exhibited CPE, the fluid was frozen at −59° C. for future use.

Brown Bullhead is a continuous cell line originally derived from the caudal trunk tissues of the catfish *Ictalurus nebulosus* (LeSeur) by R. G. Malsberger and C. P. Cerini at Lehigh University, Bethlehem, Pennsylvania. It has passaged over 140 times in vitro. Cells were grown in 50 $cm^2$ glass culture bottles and when 90% confluent, the medium was changed and the cells inoculated with virus. When CPE was present in almost the entire monolayer, the medium was harvested and stored in 1–2 ml aliquots at −59° C.

Cells were prepared for virus assay in the following manner. First, monolayers were washed with CMF twice and 0.25% trypsin was added to the vessel. After detachment, the cells were resuspended in the desired volume of culture medium and further dispersed by pipetting several times with a pro-pipet. One ml of this cell suspension was placed into individual 16×125 mm screw-capped tubes. The cells were incubated between 18° and 25° C. until they were 90–100% confluent, at which time they were used for virus titrations.

Virus samples were titrated by first diluting the sample 10-fold in Hank's Balanced Salt Solution (HBSS) (Merchant et al, supra). Exactly 0.1 ml of each virus dilution was inoculated into triplicate tubes of cells which had just had a medium change. Cultures were incubated at 25° C., examined every 3–4 days for CPE, and scored on the seventh day. Virus titrations were calculated according to the method of Reed and Muench (Rovozzo and Burke, *A Manual of Basic Virological Techniques*, Prentice-Hall, 1971).

Clarias cells used for experiments with CCV were removed from culture flasks using the standard trypsinization procedure, diluted with culture medium and seeded into 13×90 mm Leighton tubes at the rate of 1 ml of cell suspension per tube. Cell suspensions contained about $5\times10^5$ cells/ml. When the cells were 90–100% confluent, they were used for infection studies.

In order to first ascertain whether Clarias cells were susceptible to CCV in vitro, confluent Leighton tube cultures of the particular Clarias cell line under study were inoculated with $5.6\times10^3$ $TCID_{50}$ of virus. Controls included the inoculation of Clarias and BB cells with an equal volume of culture medium and BB cells with the same amount of virus.

If cells in an experimental culture began to exhibit cytopathic effect (CPE), 0.1 ml of the supernatant fluid was transferred to another culture when CPE was nearly complete. This procedure was then repeated when CPE was apparent in the new culture.

Once it had been determined that Clarias cells were susceptible to CCV, studies were initiated involving the development of viral mutants. The procedure used was similar to that used by Sabin et al (1953) for the isolation of poliovirus mutants. A Leighton tube containing Clarias cells was infected with CCV. When 90–100% of the cells exhibited CPE, 0.1 ml of the culture medium was transferred to another culture. This infection procedure was repeated when this latter culture exhibited CPE. In this manner, the virus sample was rapidly passaged at low dilution, which facilitates the emergence of mutant virus particles as the dominant population (Fenner et al, *The Biology of Animal Viruses*, Academic Press, N.Y., 1974).

After the virus had been passaged the number of times indicated below several terminal dilutions were performed in order to segregate the numerically dominant virus forms from the rest of the population. These were then tested for the desired characteristics of avirulence for Ictalurus and increased pathogenicity for Clarias. Terminal dilutions were performed in a manner similar to that of Sabin et al (J. Exptl. Med., 99: 551–76, 1953). A large amount of virus was produced by inoculating 0.1 ml of undiluted fluid from a virus infected culture into a Blake bottle containing a monolayer of Clarias cells. When CPE was complete, a sample of this virus was titrated either in Clarias cells alone or in both Clarias and BB cells. Titration in BB cells was performed in order to monitor any changes which may have occurred in the relative amounts of virus produced in the Clarias and BB systems since in vitro changes in virus production can sometimes be indicative of in vivo changes in pathogenicity and may subsequently be useful as markers of attenuation. For this same reason, comparative titrations of CCV in Clarias and BB cells were also performed at other times during the passaging procedure.

When CPE was almost completed in the terminal dilution tube of the titration carried out in Clarias cells, another terminal dilution was performed in the same manner. A total of three terminal dilutions were used for the isolation of individual virus particles. A large amount of virus was then produced by infecting a Blake bottle of Clarias cells with 0.1 ml of undiluted fluid from the third terminal dilution tube. Virus harvested from this culture was frozen in 1–2 ml aliquots at −59° C., and used for in vivo testing as described below.

Initial attempts at establishing cultures using the procedure of McKenzie and Stephenson, supra, met with some success, but a large percentage of the plated tissue fragments usually failed to adhere to the surface of the culture flask, even after two hours in an upright position. These fragments would often detach from the surface of the culture flask, even with the most careful handling. However if the tissue fragments were added directly to the flask in the presence of trypsin alone, more than 95% of all tissue pieces adhered almost instantaneously. These fragments remained firmly attached subsequent to the addition of culture medium, regardless of size. The cultures could be immediately examined after plating without fear of dislodging the fragments.

Using this technique, two cell lines were established: GD1I (gonad) and K1K (kidney). GD1I is a mixed epithelioid-fibroblastic line. K1K is a fibroblastic cell line which contains a population of dendritic, pigmented cells.

A third cell line was established from gill tissue and designated G1B. As a primary culture, only three attached explants were originally present. A small number of fibroblast-like cells migrated from their periphery. After this short period of migratory activity, the culture remained inactive for over one month. Finally, two months after initiation of the culture, rounded, epithelial-like cells began to appear scattered throughout the flask. These cells slowly increased in numbers, forming "colonies" of cells, until at seven months the culture became nearly confluent and was subcultivated.

The inoculation of Clarias cell cultures with CCV resulted in the formation of a distinctive cytopathic reaction which was transmissible both to Clarias and BB cells. K1K, GD1I and G1B continued to exhibit CPE when challenged five times in succession with a 10-fold dilution of the previously infected culture resulting in a $10^{-5}$ dilution of the original inoculum. Controls without virus were unchanged, while CCV infected BB cells also exhibited CPE. The most outstanding characteristic of this cytopathic effect is cell fusion and the formation of large, multinucleated syncytia.

In K1K and GD1I, foci of fused cells appeared within the monolayer. These foci progressively spread with time to encompass the entire monolayer, forming a syncytial network containing "islands" of nuclei scattered throughout. A very small number of phase dense, apparently unfused cells were seen distributed throughout the culture. Cytoplasmic blebs were more common in the infected cultures. The progressive fusion reaction was most easily witnessed in G1B due to the flat, plate-like morphology of this cell line. Phase light vacuoles of variable sizes were a feature of CCV infection of all three cell lines. Controls contained almost none of these vacuoles, although other forms of vacuolation not associated with virus infection were noted in G1B.

Concomitant with the fusion phenomenon was the subsequent retraction of the fused syncytial masses, as seen in virus-infected G1B cultures. In K1K and GD1I, retraction resulted in the complete detachment of the monolayer from the surface of the culture flask. In G1B cultures, the degree of cell destruction was dependent upon the amount of virus inoculum. If the relative titer was too low, foci of syncytia would appear but only a portion of the monolayer was destroyed. Sometimes this destroyed area was recolonized by healthy cells after the infective focus had completely degenerated. In K1K and GD1I, complete cell destruction always occurred, irrespecive of the titer with which a culture was infected.

CCV infection in BB cells was virtually the same as described for K1K and GD1I except that virtually no cytoplasmic blebs were present and there was very little vacuole formation.

After the demonstration of an active infection by CCV in all three Clarias cell lines, passage of CCV was continued in K1K alone. The history of this virus is shown in Table I. At the 22nd and again at the 55th passage level, a large amount of virus was prepared, which then underwent three terminal dilutions, followed by the production of a large amount of virus, which was designated V26(K1K) and V59(K1K), respectively.

TABLE I

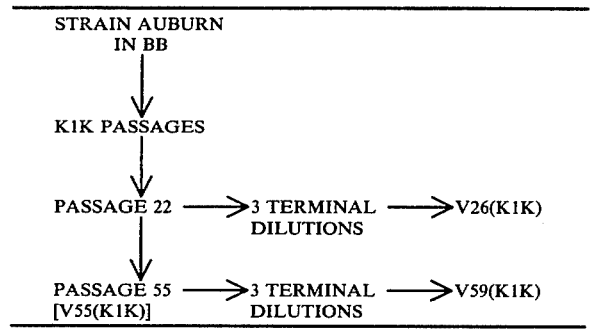

STRAIN AUBURN IN BB → K1K PASSAGES → PASSAGE 22 → 3 TERMINAL DILUTIONS → V26(K1K) → PASSAGE 55 [V55(K1K)] → 3 TERMINAL DILUTIONS → V59(K1K)

Over the span of the in vitro passages examined, there was no change in the relative sensitivity of K1K and BB cells for CCV. BB cells were consistently a more sensitive system for the detection of CCV, with titers averaging 25 times greater compared to K1K cells infected with the same viral inoculum. See Table II.

TABLE II
COMPARATIVE TITER OF CHANNEL CATFISH VIRUS AFTER PASSAGE IN CLARIAS CELL CULTURE

| Passage level in Clarias kidney cells | Titer (TDID/ml) Brown Bullhead | Titer (TDID/ml) Clarias kidney | Titer ratio (BB/CK) |
|---|---|---|---|
| 18 | $3.2 \times 10^5$ | $5.2 \times 10^4$ | 10 |
| 22 | $5.6 \times 10^6$ | $5.6 \times 10^5$ | 10 |
| 23 | $3.2 \times 10^6$ | $5.6 \times 10^4$ | 56 |
| 24 | $3.2 \times 10^6$ | $3.2 \times 10^4$ | 100 |
| 26 | $3.2 \times 10^5$ | $3.2 \times 10^4$ | 10 |
| 27 | $5.6 \times 10^4$ | $5.6 \times 10^3$ | 10 |
| 39 | $3.2 \times 10^5$ | $5.6 \times 10^4$ | 6 |
| 56 | $3.2 \times 10^6$ | $1.8 \times 10^5$ | 18 |
| 59 | $3.2 \times 10^6$ | $3.2 \times 10^5$ | 10 |

Pathogenicity Tests

Domestically raised channel catfish were tested in 36 liter aquaria with aeration provided by compressed air bubbled through box filters containing quartz gravel. Fish were fed a commercial pelleted food at a rate of 1–2% of body weight daily. After an acclimation period lasting at least 6 days, test fish were injected intraperitoneally (IP) with 0.01–0.1 ml of test suspension consisting of wild type CCV (LPV=low passage virus), Clarias cell culture-passaged CCV (HPV=high passage virus), or HBSS. Fish were examined at least once daily. Dead fish were removed from the tanks, individually wrapped in aluminum foil and frozen at −59° C. The duration of all tests was three weeks. In all tests, fish were injected with HPV which was of at least as high a titer as that of the LPV used in the same experiment.

Virus isolation from injected fish was performed as follows: The sample fish was thawed, its internal organs removed and ground in a cold (ice bath) mortar and pestle in about ten volumes of HBSS. Ten to twenty more volumes were then added and this mixture, consisting of about three ml of suspended material, was prefiltered through a coarse filter and then passed through a $0.45\mu$ filter treated with complete culture medium containing 9% fetal bovine serum. One tenth ml of this fluid was then inoculated onto two $16 \times 125$ mm test tube monolayer cultures of BB cells and incubated at 25° C. Controls consisted of HBSS inoculated tubes. Cultures were examined up to seven days for CPE.

In order to ascertain whether protection was conveyed by immunization with HPV, fish were challenged IP with LPV. The cultural conditions and inoculation protocol followed were the same as described for the pathogenicity tests. Following the first injection with either HPV or HBSS, both groups of fish were challenged with virulent LPV and mortalities tallied for three weeks. Virus isolation from injected fishes was performed as outlined in the pathogenicity tests.

Pathogenicity Tests

The mortality rate of I. punctatus injected with HPV-V59(K1K) was lower than that of fish injected with CCV(H)-2 strain LPV. This reduced pathogenicity was accentuated by the fact that between 3–20 times as much HPV was inoculated versus CCV(H)-2 for a particular test.

Immunization Tests

Fish injected with either V26(K1K) or V59(K1K) HPV strains exhibited resistance to challenge with LPV virus which was highly pathogenic for sham-inoculated fish (Table III). Mortality in these sham-inoculated fish was always 100% while that of HPV injected fish never exceeded 25%. CCV was isolated from a fish randomly selected from tests #2 and #5 while virus was isolated from one of the two fish assayed in test #1.

TABLE 3
EFFECT OF INJECTION WITH HPV UPON CHALLENGE WITH A VIRULENT LPV STRAIN

| | VACCINATION PARAMETERS | | | | | CHALLENGE PARAMETERS | | | | MORTALITY | | |
|---|---|---|---|---|---|---|---|---|---|---|---|---|
| | Inoculum (TCID$_{50}$/Fish) | | Size | Age | Temp. | Inoculum (TCID$_{50}$/Fish) | | Time Post vacc. | Temp. | | | |
| Test | V26 (K1K) | V59 (K1K) | (g) | (mo) | (C.) | CCV (A)-5 | CCV (H)-2 | (days) | (C.) | Cont[a] | V26 | V59 |
| 1 | 20 | | 3.0 | 6 | 25–27 | 56,000 | | 181 | 27–28 | 2/2 | 0/4 | |
| 2 | 4,800 | | 1.5 | 4 | 27–28 | | 54,000 | 33 | 28–30 | 5/5 | 1/4 | |
| 3 | | 8,500 | 1.5 | 4¼ | 27–28 | | 54,000 | 23 | 29–30 | 5/5 | | 1/5 |
| 4 | | 18,000 | 0.5 | 2¼ | 29–30 | | 2,700 | 24 | 29–30 | 6/6 | | 1/6 |
| 5 | | 18,000 | 0.5 | 2¼ | 29–30 | | 2,700 | 24 | 29–30 | 5/5 | | 0/5 |
| 6 | | 180,000 | 2.5 | 4¾ | 29–30 | | 54,000 | 24 | 29–30 | 3/3 | | 0/5 |

[a]Unimmunized fish, previously injected with HBSS, which were challenged with the same inoculum of LPV as vaccinees (V26 or V59).

The attenuated virus has a titer of $1.4 \times 10^6$ plaque forming units/ml, produces distinctly smaller plaque morphology on cultures of catfish host cells than the non-attenuated virus and does not induce mortality in channel catfish when injected at doses as high as 90,000 tissue culture infectious doses at 50 per fish.

The harvested attenuated virus is diluted with a pharmaceutically acceptable diluent to prepare the vaccine.

Hyperosmotic infiltration was employed to immunize the channel catfish. This procedure involves immersing the catfish in a suitable electrolyte solution, preferably 8% NaCL and thereafter immersing the channel catfish in the vaccine for a time sufficient for the vaccine to infiltrate said channel catfish.

The channel catfish are immersed in the electrolyte containing solution for a time sufficient to enhance the hyperosmotic infiltration of the vaccine into the catfish upon subsequent immersion therein, generally about 50-60 seconds.

The following describes a procedure for immunizing channel catfish against channel catfish virus disease:

I. Maintenance of Fish:

Fingerling channel catfish *Ictalurus punctatus* L. weighing an average of 4.63 gm and measuring an average of 8.7 cm are maintained in glass aquaria at a rate of 1 fish/gallon of aerated water (29 C).

Twenty-four hours prior to and following vaccination food is withheld from the fish.

II. Virus Vaccine:

An attenuated strain of channel catfish virus (V62) which had been passaged 62 times in walking catfish cells was grown to a titer of $1.4\times10^6$ plaque forming units/ml. The vaccine preparation was assayed on brown bullhead cells and kept frozen at −70 C.

III. Vaccination:

The procedure given below is for a group of 25 fish. All solutions are kept at 29 C.

Twenty-five fish are now collected into a 15 cm dia ×16 cm deep plastic container with a screen mesh bottom (dipper). This container is placed in a receptacle with 1 gallon of water. When all fish are in the dipper, it is raised, the water allowed to drain out (1–2 sec), and immediately placed in a 5 liter plastic bucket containing 2 liters of 8% sodium chloride solution. After 50–60 seconds of immersion, the dipper is raised, the salt solution allowed to drain through the screen, and the dipper containing the fish is then immersed into the vaccine solution.

The vaccine solution is prepared by taking 55 ml of a stock containing approximately 1 million plaque forming units (±10%) of V62 and mixing it with 4 L of a water-ion solution. The water-ion solution is:

1.0 gm $cacl_2.2H_2O$/liter water 1.0 gm $Mgcl_2.6H_2O$/liter water

The fish are maintained in the vaccine solution for approximately 30 min. (+5 min.). They are then poured from the dipper into maintenance aquaria.

Within about forty-five (45) to sixty (60) days following the initial vaccination it is essential that the fish be given a booster vaccination by the same above-described procedure. Within a total of sixty (60) days from the initial vaccination the fish are immune and resist challenge by injection with the virulent wild type virus.

The following table demonstrates the efficiency of the immunization procedure:

| Surviving Vaccinees following Challenge with Wild-type Virus | | |
|---|---|---|
| Vaccine + Booster* | Vaccine alone | No Vaccine |
| 97% | 30% | 22% |

*Fish were given a second vaccination or booster two months after initial vaccination. Data represents a total of 100 fish divided into three groups. Vaccination was done by immersion, challenged by intraperitoneal injection.

We claim:

1. A modified, live infectious channel catfish virus vaccine which imparts immunity from channel catfish virus disease when administered to channel catfish comprising an attenuated strain or strains of channel catfish virus and a pharmaceutically acceptable diluent.

2. The vaccine of claim 1 wherein said attenuated virus has a titer of $1.4\times10^6$ plaque forming units/ml, produces distinctly smaller plaque morphology on cultures of catfish host cells than the non-attenuated virus, does not induce mortality in channel catfish when injected at doses as high as 90,000 tissue culture infectious doses at 50 per fish.

3. The vaccine of claim 1 wherein said virus is attenuated according to a method comprising:

(a) forming a plurality of catfish tissue cell cell cultures, (b) serially passing a virulent channel catfish virus through said cultures for a plurality of passages, (c) continuing said serial passages until the resulting virus material is attenuated to permit its safe administration to channel catfish, (d) inoculating catfish tissue cells with said resulting virus material, and (e) harvesting virus material from said cells.

4. The vaccine of claim 3 wherein said catfish tissue cell cultures comprise material selected from the group consisting of gonad, kidney and gill tissue of the walking catfish.

5. The vaccine of claim 4 wherein said catfish tissue cell culture comprises walking catfish kidney tissue.

6. A method of producing an attenuated strain or strains of channel catfish virus comprising:

(a) forming a plurality of catfish tissue cell cultures, (b) serially passing a virulent channel catfish virus through said cultures for a plurality of passages, (c) continuing said serial passages until the resulting virus material is attenuated to permit its safe administration to channel catfish, (d) inoculating catfish tissue cells with said resulting virus material, and (e) harvesting attenuated virus material from said cells.

7. The method of claim 6 wherein said catfish tissue cell cultures comprise material selected from the group consisting of gonad, kidney and gill tissue of the walking catfish.

8. The method of claim 7 wherein said catfish tissue cell culture comprises walking catfish kidney tissue.

9. A method of preparing a modified, live infectious channel catfish virus vaccine which imparts immunity from channel catfish virus disease when administered to channel catfish comprising diluting the harvested virus material produced by the method of claim 6 with a pharmaceutically acceptable diluent.

10. A method of immunizing channel catfish from channel catfish virus disease comprising hyperosmotically infiltrating channel catfish with the vaccine of claim 1 and, approximately 45 to 60 days thereafter, again hyperosmotically infiltrating said channel catfish with said vaccine.

11. The method of claim 10 wherein said hyperosmotic infiltration of vaccine is effected by:

(a) immersing channel catfish in water containing a substantial concentration of electrolyte, and (b) thereafter immersing said channel catfish in said vaccine for a time sufficient for said vaccine to infiltrate said channel catfish.

12. The method of claim 11 wherein said electrolyte is sodium chloride.

13. The method of claim 12 wherein said electrolyte solution contains about 8%, by weight, of sodium chloride.

14. The method of claim 13 wherein said channel catfish are immersed in said electrolyte containing solution for a time sufficient to enhance the hyperosmotic infiltration of said vaccine into said catfish upon subsequent immersion therein.

15. The method of claim 10 wherein said channel catfish are immersed in said electrolyte containing solution for about 50 to 60 seconds.

16. The method of claim 10 wherein said channel catfish are immersed in said vaccine for a time sufficient to allow the hyperosmotic infiltration therewith of sufficient attenuated virus to immunize said channel catfish against channel catfish virus disease.

* * * * *